(12) United States Patent
Bavykin et al.

(10) Patent No.: US 6,818,398 B2
(45) Date of Patent: Nov. 16, 2004

(54) COLUMN DEVICE FOR ISOLATION AND LABELING OF NUCLEIC ACIDS

(75) Inventors: Sergei G. Bavykin, Darien, IL (US); James P. Akowski, Alexandra, VA (US); Vladimir M. Zakhariev, Moscow (RU); Andrei Mirzabekov, Darien, IL (US)

(73) Assignee: The University of Chicago, Chicago, IL (US)

(*) Notice: Subject to any disclaimer, the term of this patent is extended or adjusted under 35 U.S.C. 154(b) by 22 days.

(21) Appl. No.: 09/751,654

(22) Filed: Dec. 29, 2000

(65) Prior Publication Data

US 2003/0096229 A1 May 22, 2003

(51) Int. Cl.[7] .......................... C12Q 1/68; C07H 21/02
(52) U.S. Cl. ........................................ 435/6; 536/23.1
(58) Field of Search ................... 435/6, 270; 536/23.1, 536/25.3

(56) References Cited

U.S. PATENT DOCUMENTS 5,652,141 A * 7/1997 Henco et al. ............... 435/270
5,981,734 A * 11/1999 Mirzabekov et al. ....... 536/25.3
6,218,531 B1 * 4/2001 Ekenberg .................. 536/25.41

OTHER PUBLICATIONS

Chakrabarti et al. Fluorescent labelling of closely-spaced aldehydes induced in DNA by bleomycin–Fe(III). Int. J. Radiat. Biol., vol. 75, No. 8, pp. 1055–1065, 1999.*

Proudnikov et al. Chemical methods of DNA and RNA fluorescent labelling. Nucleic Acids Res., vol. 24(22): 4535–4542, 1996.*

Proudnikov D et al. Chemical methods of DNA and RNA fluorescent labelling. Nucleic Acids Res., vol. 24(22): 4535–4542, 1996.*

Proudnikov et al. Chemical methods of DNA and RNA fluorescent labeling. Nucleic Acids Research, vol. 24, No. 22, pp. 4535–4532, 1996.*

Eldadah et al. A new approach for the electrophoretic detection of apoptosis. Nucleic Acids Research, 24 (20): 4092–4093, 1996.*

* cited by examiner

Primary Examiner—Jeffrey Fredman
Assistant Examiner—Suryaprabha Chunduru
(74) Attorney, Agent, or Firm—Cherskov & Flaynik

(57) ABSTRACT

A method for manipulating genetic material, the method comprising disrupting cells so as to liberate genetic material contained in the cells; contacting the genetic material to a silica column in a manner to cause the genetic material to become immobilized to the column; labeling the immobilized genetic material; and eluting the labeled material from the column. Also provided is a two-buffer process for manipulating genetic material, the process comprising: contacting cells containing the genetic material to a silica column; creating a first fraction of cell detritus and a second fraction containing the genetic material; confining the genetic material to the column; removing the cell detritus; contacting the genetic material with radicals so as to produce reactive aldehyde groups on the genetic material, and attaching chromophore to the genetic material.

27 Claims, 6 Drawing Sheets

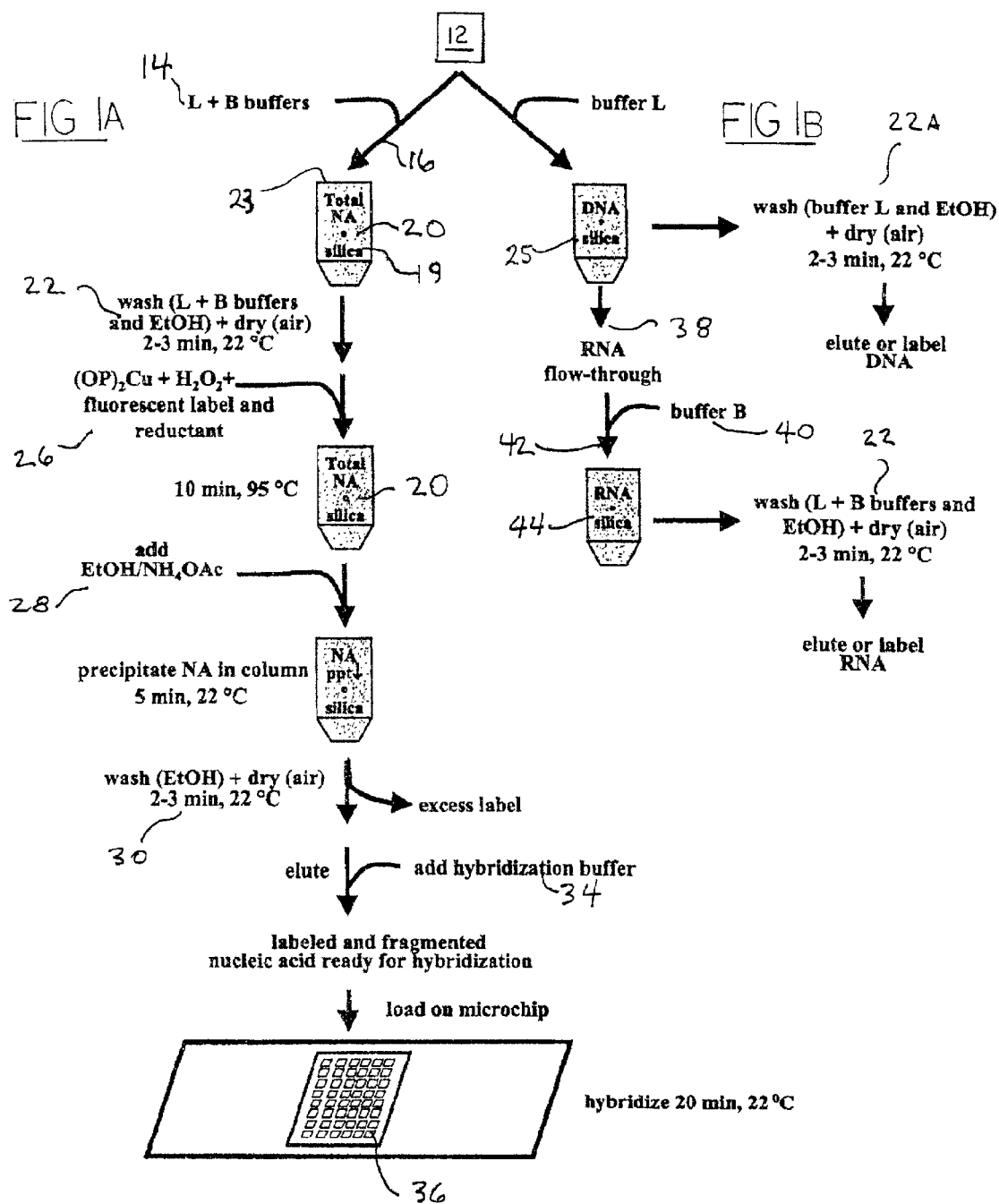

COLUMN DEVICE FOR ISOLATION AND LABELING OF NUCLEIC ACIDS

CONTRACTUAL ORIGIN OF THE INVENTION

The United States Government has rights in this invention pursuant to Contract Number W-31-109-ENG-38 between the United States Government and Argonne National Laboratory.

BACKGROUND OF THE INVENTION

1. Field of the Invention

This invention relates to a device for manipulating genetic material, and more specifically, this invention relates to a column device for isolation, fractionating, fragmentation, labeling and purification of total nucleic acid material, DNA and RNA in a minimal number of steps.

2. Background of the Invention

Traditional methods of bacterial identification are usually based on morphological and/or physiological features of a microorganism or on analysis of 16S rRNA gene sequences. These methods require considerable amounts of time.

PCR and other amplification techniques are utilized for bacteria identification. Immunological methods and mass-spectrometry also have been adapted for this purpose, but are expensive and cumbersome.

DNA microchip technology is a rapid, high throughput platform for nucleic acid hybridization reactions. However, nucleic acid fragmentation and labeling are two of the limiting steps in the development of rapid protocols for DNA/RNA microchip technology.

Several enzymatic and chemical protocols are available for fluorescent labeling of nucleic acids. All of these methods are expensive and time consuming. Lastly, most of these protocols demand careful prerequisite nucleic acid isolation, fractionation (generally requiring one or more hours), labeling, separate sample fragmentation procedures and a final purification step.

Typical nucleic acid labeling methods adopt a myriad of approaches. For example, M. D. Schena et al., *Science* 270, 467–470 (1995); J. L. DeRisi et al., *Science* 278, 680–686 (1997); G. P. Yang et al., *Nucl. Acid Res.* 27, 1517–1523 (1999); K. Wang et al., *Gene* 229, 101–108 (1999), and M. Wilson et al. *Proc. Natl. Acad. Sci USA* 96, 12833–12838 all rely on effecting labeling using reverse transcriptase. Typically, this process requires from one to two hours to complete.

D. Guiliano et al. *Bio Techniques* 27 146–152 (1999) and G. T. Hermanson, *Bioconjugate Techniques* (Academic Press, Inc. San Diego, Calif., 1996) utilize random priming. However, these protocols require from 3 to 10 hours to complete.

Terminal transferase protocols are featured in K. L. Gunderson et al. *Genome Res.* 8, 1142–1153 (1998) and L. Wodicka et al. *Nat. Biotechnol.* 15, 1359–1367. However, these processes also require between 1 and 2 hours to run.

Polymerase Chain Reaction (PCR) protocols for labeling are widespread. Typical references for PCR processes include R. J. Sapolsky et al. *Genomics* 33, 445–456 (1996); M. T. *Cronin et al. Hum. Mutat.* 7, 244–255 (1996); S. Tyagi et al. *Nat. Biotechnol* 16, 49–53 (1998); and P. N. Gilles et al. *Nat. Biotechnol* 17, 365–370 (1999). However, PCR protocols require between 1 and 2 hours to complete.

A need exists in the art for a high throughput fractionation and labeling protocol for nucleic acid materials. The protocol should require mild conditions of reaction, and decrease the number of solutions and reaction steps compared to typical protocols. The method should yield high amounts of cross-linked complexes in short incubation times. And the method should be applicable to both DNA and RNA sequences.

SUMMARY OF THE INVENTION

It is an object of the present invention to provide a method for labeling nucleotide molecules that overcomes many of the disadvantages of the prior art.

Another object of the present invention is an economical method for labeling DNA and RNA molecules. A feature of the invention is that a column, which very easily may be automated, is utilized to immobilize and subject genetic material to reaction sequences. Another feature is that fluid transport through the column can be facilitated using low speed centrifugation in the laboratory or via syringe-imparted pressure in the field. An advantage of the method is that the process is portable and can be easily juxtaposed to any arrays for subsequent analysis of hybridizations.

Yet another object of the present invention is to provide a method for modifying nucleic acid. A feature of the invention is that the modification occurs on a column in the presence of hydrogen peroxide and ultimately lead to the formation of an aldehyde group for subsequent labeling. An advantage of the present method is that the reaction is simple, requires mild conditions, and produces high yields of cross-linked complexes which are utilized in hybridization experiments.

As a result, a universal method of preparation of labeled nucleic acids samples from studied bacterial or eucaryotic cells is provided for use with any type of hybridization experiments, including microarray assays. The method allows all chemical manipulations to be provided in a minimal number of steps (typically three steps) on a single column, in a span of approximately 30 minutes.

Briefly, the invention provides a method for manipulating genetic material, the method comprising: disrupting cells so as to liberate genetic material contained in the cells; fractionating, if necessary, the genetic material so as to separate DNA from RNA, contacting the genetic material to a silica column in a manner to cause the genetic material to become immobilized to the column; separating cell detritus from the immobilized genetic material; fragmenting and labeling the immobilized genetic material; separating the labeled genetic material from excess label, and eluting the labeled material from the column.

Also provided is a two-buffer process for manipulating genetic material, the process comprising contacting cells containing the genetic material to a silica column; creating a first fraction of cell detritus and a second fraction containing the genetic material; confining the genetic material to the column; removing the cell detritus; subjecting the genetic material to radicals so as to produce reactive aldehyde groups on the genetic material; and attaching chromophore to the genetic material.

BRIEF DESCRIPTION OF THE DRAWING

The present invention together with the above and other objects and advantages may best be understood from the following detailed description of the embodiment of the invention illustrated in the drawing, wherein:

FIG. 1A is a schematic diagram of a column-based protocol for manipulating genetic material generally, in accordance with features of the present invention;

FIG. 1B is a schematic diagram of a column-based protocol for manipulating and RNA solely, in accordance with features of the resent invention;

DETAILED DESCRIPTION OF THE INVENTION

A column-based protocol for manipulating genetic material is provided herein. The column can be used alone or in combination with any microarray system. A salient feature of such a system include the invented column employed for successive DNA/RNA isolation, fractionation, fragmentation, fluorescent labeling, and removal of excess free label and short oligonucleotides. To demonstrate the efficiency of the column protocol the inventors used microarrays of immobilized oligonucleotide probes whereby the microarrays are juxtaposed at a depending end of the column; and a portable battery-powered device for imaging the hybridization of fluorescently labeled RNA fragments with the arrays.

The inventors have utilized the invented column in the above-identified configuration for 16S ribosomal RNA identification.

Figure 1C:
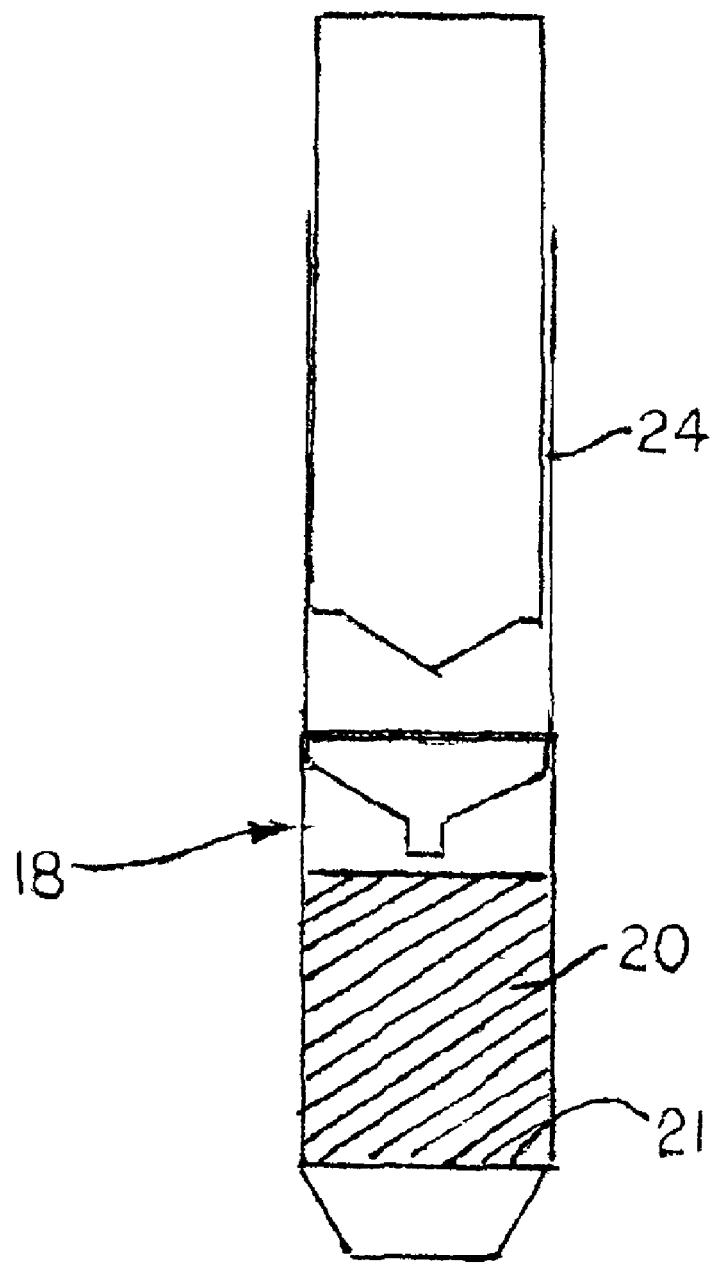
FIG. 1C is a diagram of a column positioned inferior to a column-pressurizing device, in accordance with features of the present invention.

The inventors have exploited a phenomenon that nucleic acids bind to silica in the presence of high concentration of salt. To eliminate all centrifugation steps, heretofore required in typical protocols, a syringe column configuration can be utilized. As a result of this syringe configuration (depicted in FIG. 1C), the invented column-based protocol requires only two buffers. The isolation of total nucleic acids or the fractionation of DNA/RNA is effected in 3 to 5 minutes, as opposed to the typical 60–120 minute procedures employing four or more buffers, as discussed, supra. The buffers utilized are those effecting lysis and binding of the target genetic material.

The entire mini-column procedure, from cell lysis to removal of excess fluorescent label, is executed within 20–30 minutes.

The mini-column combines a method of nucleic acid isolation utilizing guanidine thiocynanate, with a newly developed hydroxyl radical-based technique for DNA/RNA labeling and fragmentation. The chemistry of nucleic acid isolation and DNA/RNA fractionation is effected via the application of the two buffer system, outlined infra. Chemical components of the two buffer system effect differential binding of double- and single-stranded forms of nucleic acids to the silica column, thus allowing the DNA and RNA to be fractionated.

The procedure involves sequential washing of the column with different solutions. When a syringe is utilized as a means to facilitate fluid transfer through the column, no vacuum filtration steps, phenol extraction, or centrifugation are required. Any targeted eluent of the column is then hybridized with immobilized moieties on a micro-array. The overall fluorescence pattern displayed by the micro-array is captured as a digital image stationary microscope, a laser-based scanner, etc., or as a Polaroid photo.

The above-referenced three-component system was used by the inventors to discriminate *Escherichia coli, Bacillus subtilis, Bacillus thuringiensis*, and human HL60 cells.

The column device expedites processes for fractionating and labeling genetic molecules; for example, beginning with whole cells, it takes approximately 25 minutes to obtain labeled DNA/RNA samples and an additional 25 minutes to hybridize and acquire the microarray image using a stationary image analysis system or the portable imager.

Generally, the device comprises a single syringe-operated silica minicolumn. A schematic diagram of the column process is designated as numeral 10 in FIGS. 1A–1C. The column configuration centralizes three main steps in the fragmentation and isolation process.

In a first step, whole cells or pre-treated cell feed-stocks 12 are mixed with a lysis/binding buffer 14 to create a mixture 16. This mixture 16 is added to a column 18 comprising silica 20. The lysed cells 16 are allowed to contact the silica 20 for a time and at a temperature sufficient to cause genetic macromolecules from the lysed cells to adsorb to the silica 20. A myriad of times and temperatures are suitable, with typical parameters for silica binding disclosed in Boom et al. *J. Clin, Microbiol.* 28, 495–503 (1990). Detritus is passed through the column and discarded as eluent. Targeted genetic material is attached to the silica at this step and therefore is detained in the column.

The column containing the genetic material is then washed with lysis buffer and ethanol, with washing protocols 22 or 22a (elaborated below) dependent on the type of genetic material isolated. After washing, a depending end 19 of the column 18 is capped.

In a second step, the column is then heated to a selected temperature ranging from between approximately 45° C. and 100° C., mostly to evaporate any washing alcohols utilized in the previous steps. Also, it is preferred that the alcohols be removed so as to prevent their inhibition of labeling reagent. Labeling cocktail, sans hydrogen peroxide and reductant, is also subject to a short preheating step.

The column is then infused with a labeling cocktail 26 and a top 23 of the column is sealed. After the label remains in contact with the column-bound genetic material for a time sufficient to provide thorough labeling of the genetic material, a reaction terminator is applied to the column. Then, nucleic acid precipitators 28 are added to the column to facilitate adsorption of the genetic material to the silica particles in the column. In this step, nucleic acids are not bound to the silica, but rather are agglomerated. A filter means 21 at the bottom 19 of the column is provided so as to retain precipitated genetic material The filter 21 also is resistant to ethanol or other washing fluid, as discussed elsewhere in this specification. Filter paper having an average pore side of approximately 0.22 microns provides good results. Whatman PSU 0.2 centrifuge filter units are suitable candidates for filter means.

In the third step, the column is then unsealed and subjected to a washing and drying protocol 30 to remove excess label. Labeled product 32 is then eluted from the column, mixed with hybridization buffer 34, and added to a gel array 36.

FIG. 1B depicts a protocol for solely RNA/DNA isolation. Briefly, the cell sample 12 is first contacted with lysis buffer to form a lysate. The lysate is passed over a column 25 at a rate to allow DNA in the lysate to bind to the column 25. At this juncture, column eluent is unbound material such as RNA, proteins and macromolecules.

Eluent 38 from the column 25 (containing RNA) is then mixed with a binding buffer 40 to create an RNA/binder mixture 42. That mixture 42 is contacted with a second column 44. The second column 44 is subjected to a washing protocol 22 to isolate the RNA on the column. The RNA-only containing column is then treated to either elute the RNA or else label the RNA in protocols outlined infra.

Buffer Detail

The buffer system utilized is a two component system: one for lysis, the other for binding of the target genetic material. Buffer detail is disclosed in M. Beld et al., *Nucleic Acid Res.* 24 2618–2619 (1996), and incorporated herein by reference.

Generally, both buffers utilize a powerful lysing agent such as guanidine thyocianate. Guanidine thyocianate destabilizes nucleic acid duplexes and increases hybridization rates. EDTA also is present in the buffers as an inhibitor of nucleases, which are enzymes that destroy nucleic acids. The binding buffer further contains non-ionic detergents, which are necessary in stances where single stranded nucleic acids are to be bound to silica. Exemplary detergents include Trtion X-100 and $MgCl_2$. When utilized simultaneously, the lysis buffer and binding buffer is present in a ratio of approximately 9:4 volume ratio.

Exemplary concentrations of components of the buffers are disclosed infra, when specific protocols are discussed.

Column Preparation and Usage Detail

A myriad of packing materials are suitable column constituents, including, but not limited to silica, ground glass filter, pulped glass filter, HNO3-washed glass filter pulp, HNO3-washed gel, HNO3-washed diatoms, silicic acid 400 mesh silica gel, SPE-SIL and combinations thereof.

The results of various column packing substrates are depicted infra in Table 1, wherein "batch" signifies the substrate's binding ability when confined to a centrifuge test-tube and "column" signifies the substrate's binding ability in a flow-through column. Percentage yield signifies that amount of total nucleic acid isolated on the substrate.

TABLE 1

Retention Substrates for nucleic acid retention

| Substrate | Configuration | Percent Retention Of Nucleic Acid |
| --- | --- | --- |
| Silica Particles | batch | 102 |
| Ground Glass Filter | batch | 60 |
| Pulped Glass Filter | batch | 26 |
| Crushed Glass Vial | batch | 6 |
| HNO3-washed glass filter pulp | column | 56 |
| HNO3-washed gel | batch | 53 |
| HNO3-washed gel | column | 32 |
| HNO3-washed diatoms | column | 46 |
| Silicic acid | column | 50 |
| Silica particles | column | 84 |
| Glass filter in Swinnex with class filter | filtration unit | 22 |
| Fumed silica | column | 5 |
| 400 Mesh Silica Gel | batch | 42 |
| SPE-SIL | batch | 54 |
| Crushed Quartz | batch | 12 |

When silica is utilized, a size-fractionated, silica suspension prepared as described in R. Boom, et al. *J. Clin. Microbiol* 28: 495–503, and incorporated herein by reference, is suitable.

While a variety of column shapes, diameters and lengths are applicable, the following protocol is offered for illustrative purposes only, to enable the construction of a bench-top column device. Briefly, silica stored at approximately 4 C is resuspended to a 50 micro liter ($\mu l$) suspension (containing approximately 40 $\mu l$ silica). This suspension is loaded into a 25-mm-long sterile centrifuge device containing a polysulfone filter with a diameter of 6.5 mm and a pore size of 0.2 $\mu m$ (Whatman, Fairfield, N.J.). The column is washed with approximately 500 $\mu l$ of DEPC water and approximately 60–120 ml of air is forced through the column to dry.

When a syringe is utilized, the column is sealed against the end of a 10-ml syringe (element 24 in FIG. 1C) without any glue using the O-ring from a 1.5-ml screw-cap microcentrifuge tube introduced between the syringe and the top of the column, and washed once with 500 $\mu l$ of diethyl pyrocarbonate (DEPC)-treated water.

When the protocol is conducted in stationary environs, for example in a laboratory, the syringe operations can be replaced with centrifugation. In such instances, typical sedimentation forces and times are employed to effect separation of target from non-target moieties. Typically 10,000 g for 30 seconds provides good results.

To this silica mini-column is added either whole cells, DNA or RNA. The protocols for the isolation and fractionation of these various feedstocks are discussed infra.

Total Nucleic Acid Isolation Detail

A variety of cells can be lysed and manipulated via the invented column protocol, including, but not limited to gram-positive cells, gram-negative cells, eucaryotes, and human cells. For the sake of simplicity, specific bacterial strains are discussed herein. Bacterial strains *B. subtilis* B-459, *B. thuringiensis* 4Q281, and *E. coli* BL21, as well as human HL60 cells, were used as starting material.

Gram-positive cells were pretreated by incubation with 25 $\mu l$ of a lysozyme solution (100 mg/ml) at 37° C. for 5 min before lysis. A cell pellet obtained from 1 ml of log-phase bacterial ($2 \times 10^8$ to $5 \times 10^8$ cells/ml) which were grown in standard LB medium, or human HL60 cells cultures ($6 \times 10^6$ cells/ml) that were grown as described supra, was lysed by adding 550 $\mu l$ of mixture (9:4) of lysis (L) and binding (B) buffers. Buffer L was composed of 4.5 M guanidine thyocianate (GuSCN) and 100 mM EDTA (pH 8); buffer B contained 4 M GuSCN, 135 mM Tris—HCl (pH 6.4), 3.5% (wt/vol) Triton X-100, 17.5 mM EDTA, and 215 mM $MgCl_2$. The lysate was applied to a silica mini-column, which was washed by using centrifugation (10,000 g, 30 sec.) or via the syringe 24 (twice with 0.5 ml of the L/B mixture (9:4), twice with 0.5 ml of 70% (vol/vol) ethanol, and once with 0.5 ml of 100% ethanol). The column was dried by forcing 5 ml of air through the column with the syringe 24. The bound nucleic acids were either eluted from the column by passing through same 2×60 μl of 1 mM HEPES (pH 7.5) or directly subjected to labeling/fragmentation.

RNA/DNA Isolation and Fractionation Detail

A cell pellet obtained from 1 ml of log-phase culture was lysed by the addition of 450 μl of buffer L (Gram-positive cells were pretreated with lysozyme as described above). DNA was isolated by passing the lysate over the syringe-column, allowing DNA to bind to the silica. Buffer B (200 μl) was added to the flow-through RNA fraction, which was then applied to the analogous fresh column. The first column containing bound DNA was washed five times with 0.5 ml of buffer L, twice with 0.5 ml of 70% (vol/vol) ethanol, and once with 0.5 ml of 100% (vol/vol) ethanol. The second column containing bound RNA was washed twice with 0.5 ml of the L/B mixture (9:4), and ethanol as described for isolation of total nucleic acids (see previous section). Fractionated DNA or RNA was either eluted as described above, or directly subjected to labeling/fragmentation on the column.

Column-Labeling, -Fragmentation and -Hybridization Detail

The following protocol pertains to a specific sized column, as outlined supra. As such, while the fluid volumes are specific, a technician skilled in the art of laboratory science can scale the volumes up to industrial-scale operations.

The silica column containing bound RNA, DNA, or both was sealed at the bottom with a cap from a microcentrifuge tube and pre-heated in a sand bath at 95° C. for 2 min. Freshly prepared (heated for approximately 95 C for 30 seconds) labeling cocktail (132 μl) containing 5 μl of 150 mM 1, 10-phenanthroline, 5 μl of 15 mM $CuSO_4$, 1 μl 100 mg/ml Lissamine rhodamine B ethylenediamine (Molecular Probes, Inc., Eugene, Oreg.), and 121 μl of 25 mM sodium phosphate (pH 7.0), was mixed with 3 μl 200 mM $H_2O_2$ and 15 μl 200 mM $NaCNBH_3$ and immediately applied to the minicolumn. The column was then sealed to prevent evaporation. After incubation for 10 min at 95° C., the reaction was stopped by adding 2.7 μl of 500 mM EDTA (pH 8.0). Nucleic acids were precipitated on the column by adding 17.3 μl of 3 M sodium acetate and 540 μl of cold (approximately 4 C) 100% (vol/vol) ethanol, followed by a 5-min incubation at room temperature.

Excess fluorescent label was removed by washing the column twice with 1.5 ml of 100% (vol/vol) ethanol. The column was then dried with forced air. The labeled product was eluted twice with 45–60 μl of 1 mM HEPES (pH 7.5). The eluant was adjusted to contain 5 mM EDTA, 1 M GuSCN, and 50 mM HEPES (pH 7.5) and filtered through a 0.45-μm Millex-HV syringe filter (Millipore, Bedford, Mass.).

The resulting solution (30 μl) containing 5 to 15 μg of nucleic acids, including 1 to 3.5 μg of 16S rRNA, was applied to the oligonucleotide microarray covered with a 0.5-mm-deep, 13-mm-diameter CoverWell gasketed incubation chamber (Grace Bio-Labs, Inc., Bend, Oreg.) and incubated for 20 min at room temperature.

Chemical Fragmentation and Labeling Detail

The column device is used in conjunction with the inventors' method for using redox-reactive coordination complexes to fragment and label RNA and DNA. The developed protocol can be used for both DNA and RNA-non-specific fragmentation and labeling.

Specifically, the inventors have utilized oxidants, which have free radical characteristics, to facilitate the labeling of nucleic acids. The advantages of the radical-mediated labeling methods are simplicity and high speed. In addition, the reactions are run at any temperature selected below the boiling point of water, and preferably from between 30° C. and 100° C.

The inventors have determined that redox-active coordination complexes such as OP—Cu and Fe-EDTA can be effectively used for sequence-independent nucleic acid fragmentation and labeling with fluorescent dyes as part of a DNA microchip protocol. Radicals generated with OP—Cu and Fe-EDTA effectively attack both DNA and RNA.

A myriad of coordination complexes are utilized in the invented method, including, but not limited to, 1,10-phenanthroline-Cu(II) (hereinafter referred to as OP—Cu), bleomycin-Fe(III) (hereinafter referred to as BLM-Fe), EDTA-Fe, ascorbic acid-Cu, methylene-blue-Cu, metallogporphyrins, and other chemical nucleases. These radical producing complexes facilitate amine-hydrazide-nucleic acid crosslinking. For example, in the presence of hydrogen peroxide, the BLM-Fe complex catalyzes the formation of free nucleic acid bases and the aldehyde form of deoxyribose at the abasic site of the DNA backbone. The backbone typically undergoes scission in the presence of alkali or amines.

Generally, the invention embodies a two step method for labeling DNA and RNA molecules with compounds containing primary amines. First, DNA or RNA is modified with radicals produced via a reaction between hydrogen peroxide and a coordination complex. These radicals attack the nucleic acids, resulting in the formation of the aldehyde forms of ribose or deoxyribose (See Equation 1).

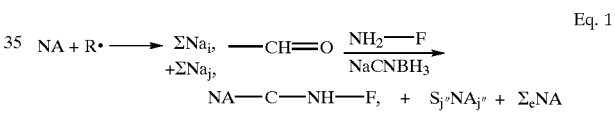

Eq. 1 wherein NA designates nucleic acid, R. is the product of a chemical radical production, of the type discussed supra, $NH_2$—F is a fluorescent dye F conjugated with primer containing primary amine, $NaCNBH_3$ is a reducing agent, $\Sigma Na_j$, —CH=O depicts an intermediate nucleic-acid form containing the aldehyde or ketone moiety, typically on the 5' carbon or on the sugar (ribose) itself. The reactive aldehyde- or ketone-group on the DNA and RNA thus serves in the second step of the method as the substrate for subsequent labeling reactions.

In the second step of the method, a primary amine is combined with the aldehyde- or ketone-group in a condensation reaction to produce a Schiff base or amides. The Schiff base is reduced and the product of this reduction step is labeled with a desirable tag. Alternatively, and as depicted above in Equation 1, the reduction and labeling step can be combined. The reduction and/or labeling processes can be done in aerobic or anaerobic conditions.

The invented method produces high yields of crosslinked complexes. It is only slightly dependent on the nucleic acid sequence or reaction temperature. The same invented protocol can be utilized to label both DNA and RNA. The resulting labeled products are effective probes in hybridization experiments.

Figure 2:
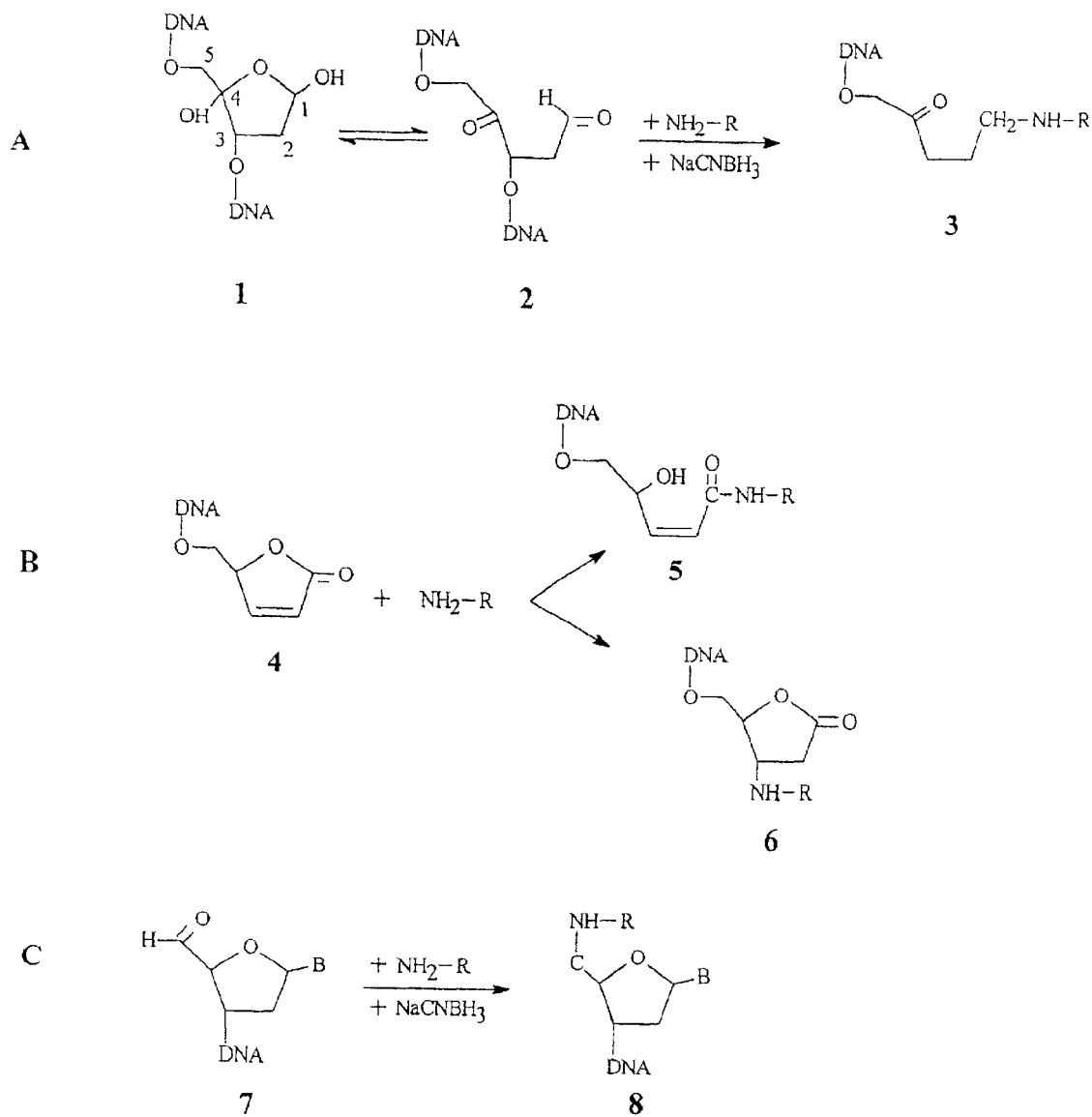
FIG. 2A depicts oxidative cleavage of DNA, in accordance with features of the present invention.
FIG. 2B depicts a DNA intermediate in a labeling sequence, in accordance with features of the present invention.
FIG. 2C depicts a DNA-based aldehyde in a labeling sequence, in accordance with features of the present invention.
Figure 3:
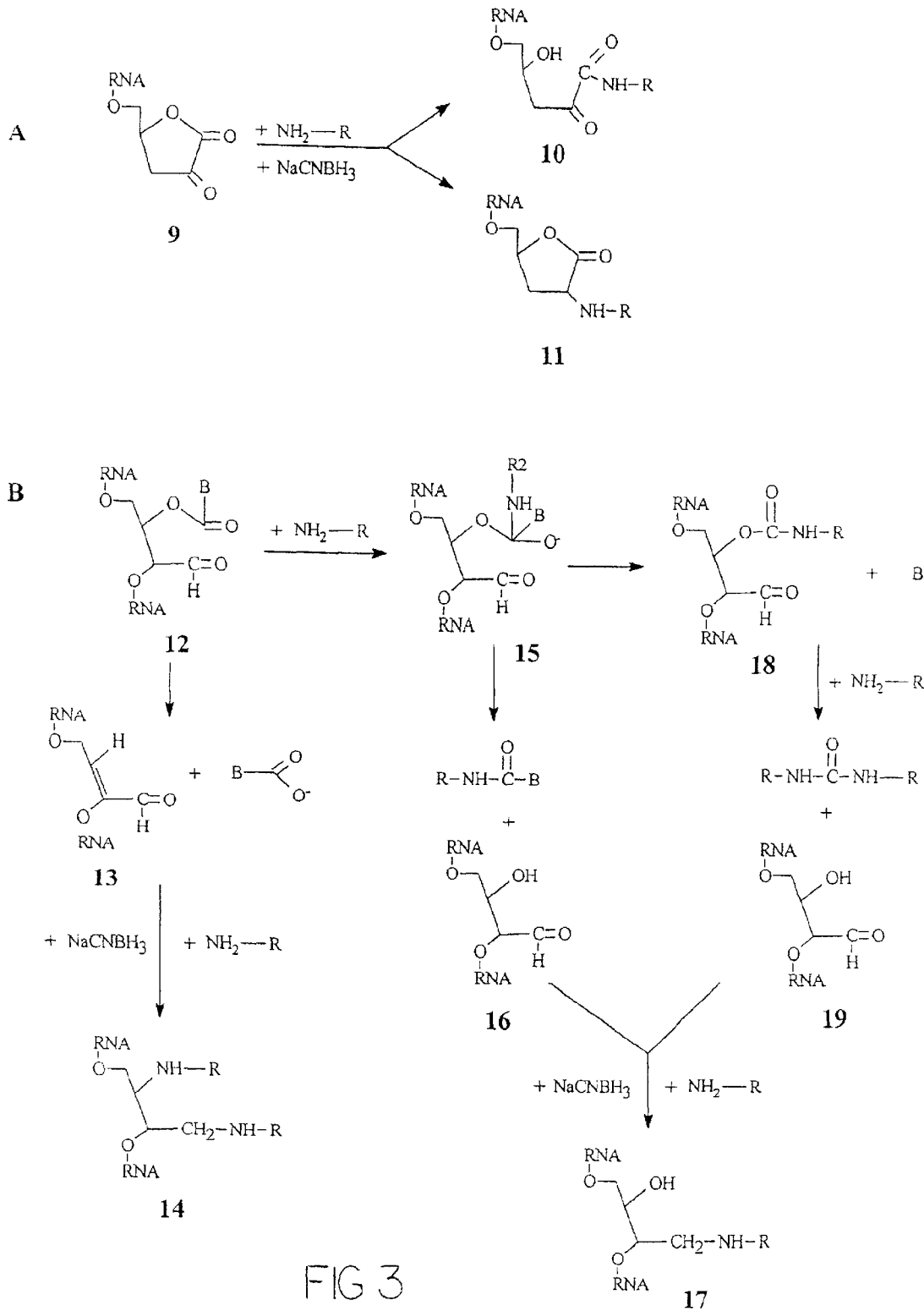
FIG. 3A depicts an RNA-based lactone in a labeling sequence, in accordance with features of the present invention.
FIG. 3B depicts an RNA-based cross-linking substrate used to form labeled product, in accordance with features of the present invention.

FIGS. 2 and 3 depict the mechanisms for dye cross linking to modified DNA and RNA, respectively. Hemiacetal, lactone, and 5'-aldehyde are the common intermediates in the oxidative strand scission of nucleic acids by radical-generating agents. These intermediates appear after base elimination has occurred and they may serve as cross-linking sites for primary amines in the invented radical-mediated nucleic acid labeling procedure.

As depicted in FIG. 2A, five carbon atoms of the DNA sugar residue have a total of seven hydrogen atoms available for abstraction by an oxidizing agent. The main pathway of DNA cleavage by OP—Cu is H-1 abstraction. OP—Cu also cleaves DNA with H-4 abstraction. OP—Cu degradation is associated with some slight sequence specificity.

The Fe-EDTA complex is negatively charged and so does not interact directly with the DNA molecule. Instead, the Fe-EDTA complex, in the presence of hydrogen peroxide, produces hydroxyl radicals which have no charge and are therefore able to diffuse into the molecule. Abstraction of the H-4 and H-5 are the predominant pathways. Preference for individual hydrogen atoms was H-5>H-4>H-2=H-3>H-1.

H-4 abstraction under anaerobic conditions results in nucleobase release with the production of a hemiacetal intermediate (FIGS. 2A,1) that is in equilibrium with the aldehyde form of deoxyribose (FIGS. 2A,2). Anaerobic conditions were utilized to optimize amine cross-linking. Generally, oxygen was reduced in reactants and reactant solutions by bubbling with argon. The inventors found that, at least for OP—Cu oxidation protocols, a 15 percent increase in hybridization signal was realized when anaerobic conditions were utilized.

The aldehyde group generated by the initial oxidation step is attacked by a nucleophilic moiety (such as a primary amine or a hydrazide), creating a reversible covalent bond (Schiff base). The resultant imine undergoes spontaneous conversion with the 3'phosphodiester bond cleaved by the mechanism of β-elimination. This facilitates the simultaneous cross-linking of amine or hydrazine derivatives of the fluorescent dyes to the modified DNA at the same time as fragmentation occurs.

After fragmentation and cross-linking, reduction of the Schiff base with sodium cyanoborohydride is desirable for production of the final labeled product, (FIG. 2A,3). This prevents removal of the cross-linked dye by δ-elimination.

Figure 5:
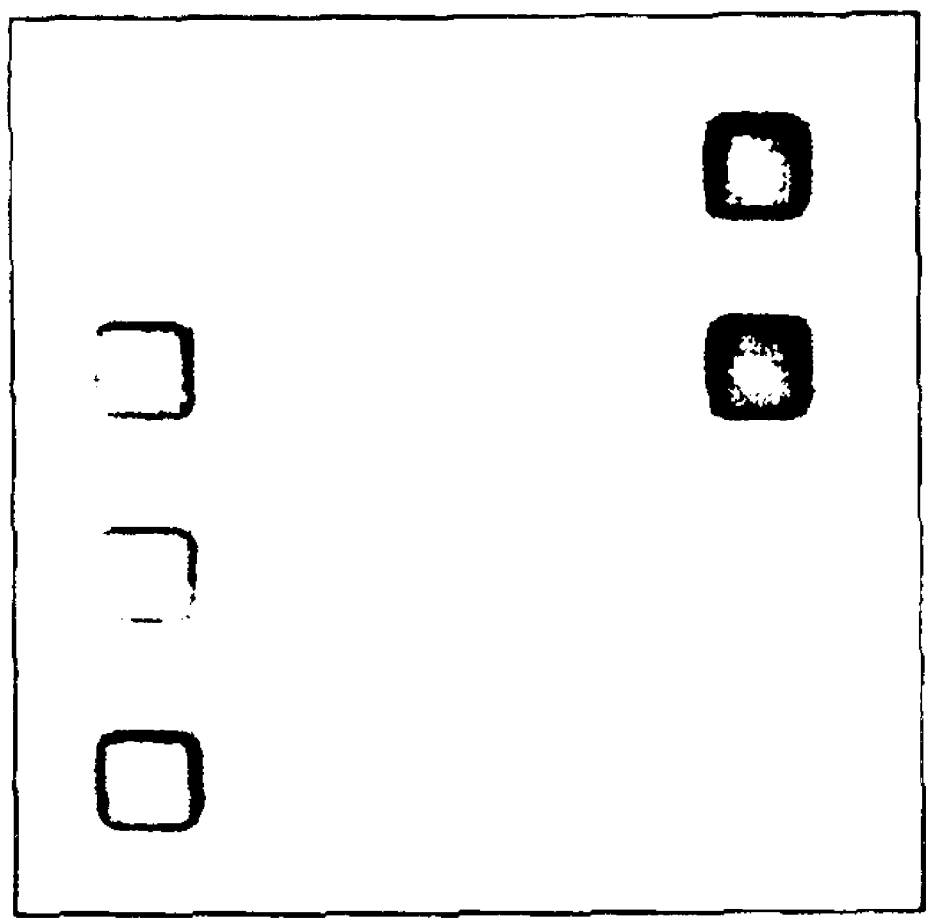
FIG. 5 is a diagram of a gel matrix depicting the efficiency of bacterial labeling utilizing features of the present invention.

Another DNA intermediate used for labeling with amino-derivatives of fluorescent dyes is meta-stable lactone in FIG. 2B. Reaction of this lactone with a primary amine leads to two stable labeled products, (FIGS. 2B,5, 6).

The H-5' abstraction pathway under both aerobic and anaerobic conditions results in the production of an oligonucleotide 5'-aldehyde, as depicted in FIG. 2, C. In one scenario, the aldehyde reacts with amines through the formation of a Schiff base in the same manner as described for the anaerobic pathway depicted in FIG. 2A. In this labeling reaction, the presence of sodium cyanoboro-hydride in the reaction buffer or immediate sodium cyanoborohydride treatment following Fe-EDTA treatment is desirable for fast Schiff base reduction and subsequent production of a stable covalent complex 8.

FIG. 3 depicts differences in labeling protocol between DNA and RNA. Specifically, the presence of the hydroxyl group in the 2'-position of ribose results in the production of α-oxa-γ-lactone, (FIGS. 3A,9) instead of lactone 4 (of FIGS. 2B,4) produced in the DNA manipulation. This lactone is able to react with primary amines to form an amide (FIGS. 3A, 10), or a Schiff base with an aldehyde group. The Schiff base then can be reduced to produce a stable complex (FIG. 3A, 11). Alternatively, a putative intermediate (FIGS. 3B, 12) serves as a substrate for cross-linking with primary amines to form stable labeled products (FIGS. 3A, 14 and 17).

The inventors have found that linking the dye to the end of the nucleic acid fragment is more useful than having the dye randomly localized along the fragment. Having the dye at the end of the fragment causes minimal steric interference during subsequent hybridization. The invented method of using radical mediated labeling is an effective method for placing the majority of the dye on the ends of the nucleic acid fragments.

In summary, radical mediated labeling results in the cross-linking of the flourescent dye to the 5'- or 3'-end of the nucleic acid strand, as depicted in FIGS. 2 and 3.

Oligonucleotide Synthesis and Array Fabrication Detail

Oligonucleotide microarrays were constructed with 10 oligonucleotide probes, each approximately 20 bases in length, with the following sequences (5'→3'): EU1, ACCGCTTGTGCGGGCCC; (SEQ. ID. NO. 1) EU2, TGCCTCCCGTAGGAGTCT; (SEQ. ID. NO. 2) U1, GATATTACCGCGGCTGGCTG; (SEQ. ID. NO. 3); U2, ACGGGCGGTGTGTAGCAA; (SEQ. ID. NO. 4); BSG1, ATTCCAGCTTCACGCAGTC; (SEQ. ID. NO. 5) BSG2, ACAGATTTGTGGGATTGGCT; (SEQ. ID. NO. 6) BS1, AAGCCACCTTTTATGTTTGA; (SEQ. ID. NO. 7) BS2, CGGTTCAAACAACCATCCGG; (SEQ. ID. NO. 8) BCG1, CGGTCTTGCAGCTCTTTGTA; (SEQ. ID. NO. 9) BCG2 (SEQ. ID. NO. 10), CAACTAGCACTTGTTCTTCC. Each potential probe was tested against all available 16S rRNA sequences (GenBank and RDP) by a function that estimates the relative duplex stability according to the number and position of mismatches.

If the 16S rRNA of any microorganism that did not belong to the genus of interest formed stable duplexes with any oligonucleotide considered as a potential probe for the microchip, this oligonucleotide was excluded from the list of probes. Oligonucleotides were synthesized with a 394 DNA/RNA Synthesizer (Perkin Elmer/Applied BioSystems, Foster City, Calif.) using standard phosphoramidite chemistry. 5¢-Amino-Modifier C6 (Glen Research, Sterling, Va.) was linked to the 5¢-end of oligonucleotides. The microarray matrix containing 100'100'20-mm polyacrylamide gel pads fixed on a glass slide and spaced by 200 mm from each other was manufactured using photopolymerization D. Gushin, *Anal. Biochem.* 250, 203–211, and incorporated herein by reference, and activated as described in D. Proudnikov et al. *Anal. Biochem.* 259, 34–41, which is also incorporated herein by reference.

Predetermined aliquots of individual 1 mM amino-oligonucleotide solutions were applied to each gel pad, containing aldehyde groups. Schiff bases coupling the oligonucleotides with aldehyde groups within the gel pads were stabilized by reduction with $NaCNBH_3$ as described herein, and also in Timofeev et al. *Nucl. Acids Res.* 24, 3142–3148 (1996), incorporated herein by reference.

EXAMPLE 1

Hybridization of Total NA Labeled With OPCu Using Oligo Microarray

Up to 70 percent of total bacterial nucleic acid is rRNA. Therefore rRNA analysis is a common, sensitive and relatively simple method of bacterial identification.

Figure 4:
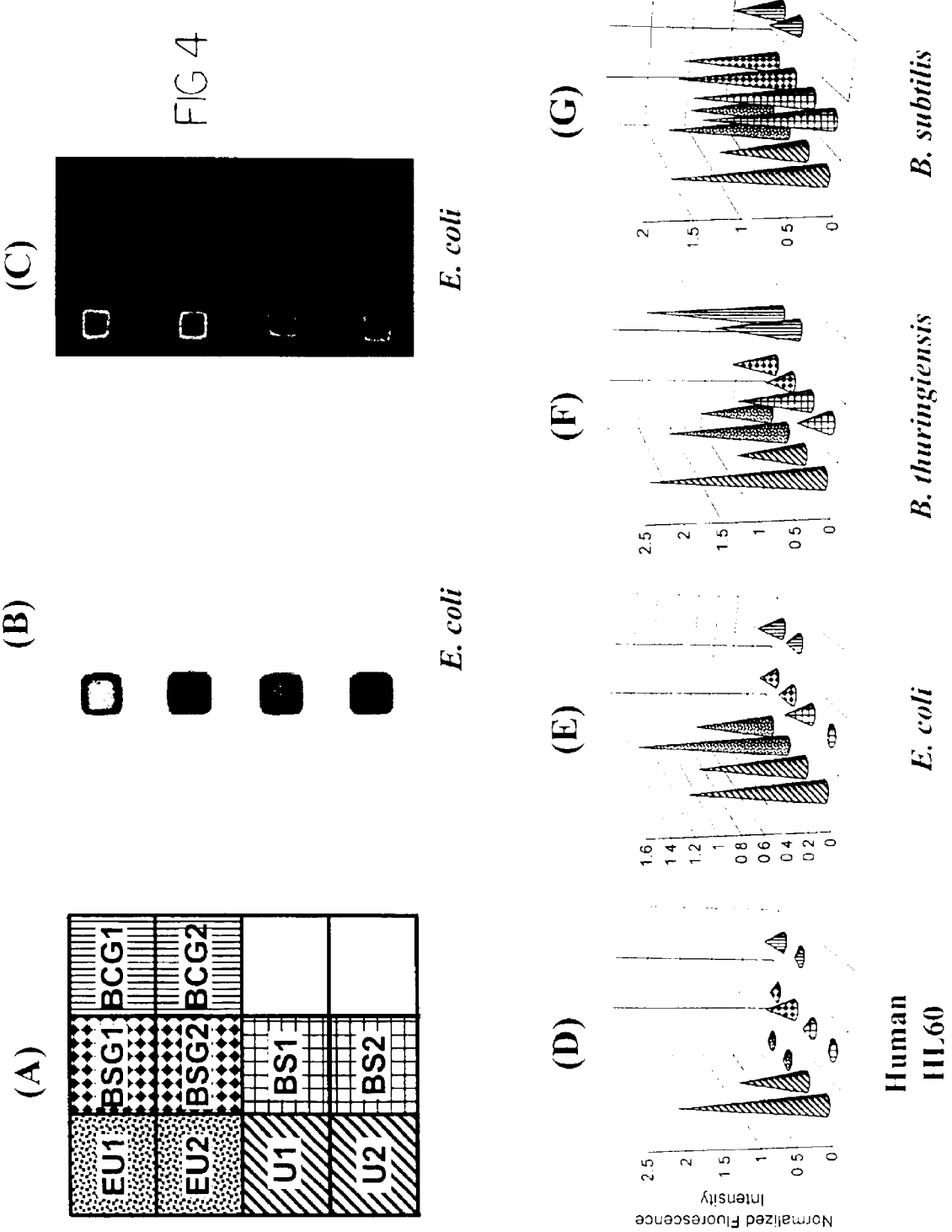
FIGS. 4A–G is a depiction of the hybridizations resulting from operation of the invented column process.

FIG. 4 depicts the results when total nucleic acids are labeled with OP—Cu using the invented column device. FIG. 4A depicts the arrangement of the probes (having the sequences disclosed above) on the micro array. U1 and U2 represents "all life" (i.e., these probes screen for all procaryotic and eucaryotic cells except for some archibacteria). EU1 and EU2 represents all eubacteria. BSG1 and BSG2 represents *B. subtilis* group bacteria. BS1 and BS2 represents *B. subtilis* sp. BCG1 and BCG2 represents cereus group bacteria.

FIG. 4B depicts the analysis of *E. coli* hybridization with a stationary microscope.

FIG. 4C depicts the same analysis using a portable imager. Normalized fluorescent signal intensities for labeled HL60 cells are depicted in FIG. 4D. Normalized intensities for *E. coli* are depicted in FIG. 4E. Signal intensities for *B. thuringiensis* and *B. subtilis* are depicted in FIGS. 4F and G, respectively. Fluorescent intensities were quantified using "Image", a custom LabView™ program available through National Instruments, Austin, Tex.

EXAMPLE 2

Hybridization of Total NA Labeled with Fe-EDTA with Microarray

Example 2 provides data wherein a FeEDTA labeling method is used with the invented column protocol and device. Unlike the OP—Cu protocol, the FeEDTA method does not depend on the presence of reducing agents in the labeling cocktail.

Freshly prepared cocktail (135 $\mu$l) containing 30 $\mu$l of 5 mM EDTA/2.5 mM ammonium iron (II) sulfate, 1 $\mu$l 100 mg/ml Lissamine rhodamine B ethylenediamine, 30 $\mu$l sodium phosphate (ph 7.0) and 74 $\mu$l DEPC-treated $H_2O$ was preheated 95° C. for 30 sec. 15 $\mu$l of 100 mM $H_2O_2$ was added and immediately applied on the column containing total nucleic acids isolated from *B. thuringiensis* str. 4Q281.

All other procedures were identical as in the OP—Cu protocol. Results of this hybridization is depicted in FIG. 5.

The microarray depicted in FIG. 5 is identical to the immobilized gel sequence arrangement depicted in FIG. 4. As can be noted, the entire first column of the array, from top to bottom (i.e., EU1, EU2, U1, and U2), is illuminated. Also, the first two cells in the third column from top to bottom (i.e., BSG1 and BSG2) are illuminated.

In summary, a procedure has been developed for nucleic acid isolation, labeling, and fragmentation within a single syringe-operated silica minicolumn. The process requires no vacuum filtration step, phenol-chloroform extraction, CsCl fractionation or centrifugation. This syringe-operated format is useful for field conditions. Alternatively, the syringe-based protocols can be replaced with centrifugation separations when the column protocol is utilized in laboratory settings. There are three main steps to the column protocol: 1) cell lysis and nucleic acid isolation; 2) fluorescent labeling and fragmentation of nuclei acids (whereby DNA or RNA can be labeled using the same protocol); and 3) the removal of short oligonucleotides and unbound dye from the column.

While the invention has been described with reference to details of the illustrated embodiment, these details are not intended to limit the scope of the invention as defined in the appended claims.

---

The embodiment of the invention in which an exclusive property or privilege is claimed is defined as follows:

1. A method for manipulating genetic material, the method comprising:
   a) disrupting cells so as to liberate genetic material contained in the cells;
   b) contacting the genetic material to a column in a manner to cause the genetic material to become immobilized to the column;
   c) fragmenting and labeling the immobilized genetic material; within the column at the same time via a free radical-mediated process, whereby free radicals facilitate oxidative strand scission of nucleic acids within the genetic material, resulting in the formation of the aldehyde forms of ribose or deoxyribose; and
   d) eluting the labeled material from the column, wherein the method occurs within 20 minutes.

2. A method for labeling genetic material, the method comprising:
   a) disrupting cells so as to liberate genetic material contained in the cells;
   b) contacting the genetic material to a column in a manner to cause the genetic material to become immobilized to the column;
   c) fragmenting and labeling the immobilized genetic material at the same time via a free radical-mediated procedure, whereby free radicals cause oxidative strand scission of nucleic acids in the genetic material; and
   d) eluting the labeled material from the column wherein the step of labeling the genetic material further comprises maintaining the column at a temperature of between 45° C. and 100° C.

3. The method as recited in claim 1 wherein the column comprises a means for subjecting the silica to pressure.

4. The method as recited in claim 3 wherein the pressure means is a syringe.

5. A method for labeling genetic material, the method comprising:
   a) disrupting cells so as to liberate genetic material contained in the cells;
   b) contacting the genetic material to a column in a manner to cause the genetic material to become immobilized to the column;

c) fragmenting and labeling the immobilized genetic material at the same time; and d) eluting the labeled material from the column wherein the step of labeling the genetic material comprises:

e) contacting double-stranded nucleic acid molecules of the genetic material with free radical-generating complexes for a time and at concentrations sufficient to produce free-aldehyde moieties via oxidative strand scission of nucleic acid in the genetic material;

f) reacting the aldehyde moieties with amine to produce a condensation product; and g) contacting the condensation product with a chromophore.

6. The method as recited in claim 5 wherein the step of contacting the condensation product with a chromophore further comprises reducing the condensation product and cross-linking the reduced condensation product with the chromophore in one reaction step.

7. The method as recited in claim 1 wherein the column is a solid substrate selected from the group consisting of silica, ground glass filter, pulped glass filter, HNO3-washed glass filter pulp, HNO3-washed gel, HNO3-washed diatoms, silicic acid 400 mesh silica gel, SPE-SIL and combinations thereof.

8. A two-buffer process for labeling genetic material, the process comprising:

a) contacting cells containing the genetic material to a silica column;

b) creating a first fraction of cell detritus and a second fraction containing the genetic material;

c) confining the genetic material to the column;

d) removing the cell detritus;

e) subjecting the genetic material to free radicals, wherein the free radicals facilitate oxidative strand scission of nucleic acids in the genetic material so as to produce reactive aldehyde groups on the genetic material; and f) attaching chromophore to the genetic material while the material resides in the column.

9. A two-buffer process for labeling nucleic acids, the process comprising:

a) contacting cells containing the nucleic acids to a silica column;

b) creating a first fraction of cell detritus and a second fraction containing the nucleic acids;

c) confining the nucleic acids to the column;

d) removing the cell detritus;

e) subjecting the nucleic acids to free radicals to facilitate oxidative strand scission of the nucleic acids so as to produce reactive aldehyde groups on the genetic material; and f) attaching chromophore to the genetic material wherein the genetic material is contacted with radical in aerobic conditions wherein the steps of attaching chromophore occurs at the same time that the reactive aldehyde groups are produced.

10. A two-buffer process for isolation of genetic material, followed by labeling of the genetic material, the process comprising:

a) contacting cells containing the genetic material to a silica column;

b) creating a first fraction of cell detritus and a second fraction containing the genetic material;

c) confining the genetic material to the column;

d) removing the cell detritus;

e) subjecting the genetic material to free radicals to facilitate oxidative scission of nucleic acids in the genetic material so as to produce reactive aldehyde groups on the genetic material; and f) attaching chromophore to the genetic material wherein the genetic material is contacted with radical in anaerobic conditions, wherein the steps of attaching chromophore occurs at the same time that the reactive aldehyde groups are produced.

11. The process as recited in claim 8 wherein the step of creating a fraction of cell detritus and the genetic material comprises contacting the cells with a lysis buffer.

12. The process as recited in claim 8 wherein steps a) through f) occur in approximately 20 minutes.

13. A two-buffer process for isolation of genetic material, followed by labeling of the genetic material, the process comprising:

a) contacting cells containing the genetic material to a silica column;

b) creating a first fraction of cell detritus and a second fraction containing the genetic material;

c) confining the genetic material to the column;

d) removing the cell detritus;

e) subjecting the genetic material to free radicals, whereby the free radicals facilitate oxidative strand scission of nucleic acids in the genetic material so as to produce reactive aldehyde groups on the genetic material; and f) attaching chromophore to the genetic material wherein the two buffers comprise a first buffer to lyse the cells and a second buffer to attach the genetic material to the column, wherein the steps of attaching chromophore occurs at the same time that the reactive aldehyde groups are produced.

14. The process as recited in claim 13 wherein the first buffer and second buffer contain guanidine thyocianate and EDTA.

15. The process as recited in claim 13 wherein the first buffer and the second buffer contact the cells simultaneously.

16. The process as recited in claim 8 wherein the genetic material is bound to chromophore in aerobic conditions.

17. The process as recited in claim 8 wherein the genetic material is bound to chromophore in anaerobic conditions.

18. The process as recited in claim 13 wherein the first buffer and the second buffer are present in a relative weight ratio of 9:4.

19. The process as recited in claim 8 wherein the temperature is maintained at 95° C.

20. The method as recited in claim 2 wherein the column comprises a means for subjecting the silica to pressure.

21. The method as recited in claim 1 wherein the step of labeling the genetic material comprises:

a) contacting nucleic acid molecules of the genetic material with radical-generating complexes for a time and at concentrations sufficient to produce free-aldehyde moieties;

b) reacting the aldehyde moieties with amine to produce a condensation product; and c) contacting the condensation product with a chromophore.

22. The method as recited in claim 21 wherein the step of contacting the condensation product with a chromophore further comprises reducing the condensation product and cross-linking the reduced condensation product with the chromophore in one reaction step.

23. The process as recited in claim 9 wherein the genetic material is bound to chromophore in aerobic conditions.

24. The process as recited in claim 10 wherein the genetic material is bound to chromophore in anaerobic conditions.

25. The process as recited in claim 8 wherein the two buffers comprise a first buffer to lyse the cells and a second buffer to attach the genetic material to the column.

26. A process for fragmenting and labeling DNA and RNA contained in a lysate, the process comprising:
   a) contacting the lysate with a first column packed with material so as to confine the DNA to the first column and allow the RNA to pass through the first column;
   b) contacting the passed through RNA to a second column packed with material so as to confine the RNA to the second column;
   c) subjecting the confined DNA and confined RNA to free radicals, whereby the free radicals facilitate oxidative strand scission of the DNA and RNA so as to produce reactive aldehyde groups on the DNA and RNA;
   d) attaching chromophore to the DNA and RNA wherein the steps of attaching chromophore occurs at the same time that the reactive aldehyde groups are produced; and
   e) eluting the DNA from the first column and the RNA from the second column, wherein a first buffer is utilized to lyse cells containing the DNA and RNA and also to attach the DNA to the first column and a second buffer is used to attach RNA to the second column.

27. The process as recited in claim 26 wherein the entire process occurs within 20–30 minutes.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 17 bases
      (B) TYPE: nucleic acid
      (C) STRANDEDNESS: Not Applicable
      (D) TOPOLOGY: linear (ii) MOLECULE TYPE: Genomic DNA (iii) HYPOTHETICAL: yes (xi) SEQUENCE DESCRIPTION: SEQ ID NO: 1:

ACCGCTTGTG CGGGCCC                          17

(2) INFORMATION FOR SEQ ID NO: 2:

(i) SEQUENCE CHARACTERISTICS:
      (A) LENGTH: 18 bases
      (B) TYPE: nucleic acid
      (C) STRANDEDNESS: Not Applicable
      (D) TOPOLOGY: linear (ii) MOLECULE TYPE: Genomic DNA (iii) HYPOTHETICAL: yes (xi) SEQUENCE DESCRIPTION: SEQ ID NO: 2:

TGCCTCCCGT AGGAGTCT                         18

(2) INFORMATION FOR SEQ ID NO: 3:

(i) SEQUENCE CHARACTERISTICS:
      (A) LENGTH: 20 bases

```
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 3:

GATATTACCG CGGCTGGCTG                                              20

(2) INFORMATION FOR SEQ ID NO: 4:

(i) SEQUENCE CHARACTERISTICS:
        (A) LENGTH: 18 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 4:

ACGGGCGGTG TGTAGCAA                                                18

(2) INFORMATION FOR SEQ ID NO: 5:

(i) SEQUENCE CHARACTERISTICS:
        (A) LENGTH: 19 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 5:

ATTCCAGCTT CACGCAGTC                                               19

(2) INFORMATION FOR SEQ ID NO: 6:

(i) SEQUENCE CHARACTERISTICS:
        (A) LENGTH: 20 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 6:

ACAGATTTGT GGGATTGGCT                                              20

(2) INFORMATION FOR SEQ ID NO: 7:

(i) SEQUENCE CHARACTERISTICS:
        (A) LENGTH: 20 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 7:

AAGCCACCTT TTATGTTTGA                                              20
```

(2) INFORMATION FOR SEQ ID NO: 8:

(i) SEQUENCE CHARACTERISTICS:
        (A) LENGTH: 20 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 8:

CGGTTCAAAC AACCATCCGG      20

(2) INFORMATION FOR SEQ ID NO: 9:

(i) SEQUENCE CHARACTERISTICS:
        (A) LENGTH: 20 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 9:

CGGTCTTGCA GCTCTTTGTA      20

(2) INFORMATION FOR SEQ ID NO: 10:

(i) SEQUENCE CHARACTERISTICS:
        (A) LENGTH: 20 bases
        (B) TYPE: nucleic acid
        (C) STRANDEDNESS: Not Applicable
        (D) TOPOLOGY: linear (ii) MOLECULE TYPE: Genomic DNA (iii) HYPOTHETICAL: yes (xi) SEQUENCE DESCRIPTION: SEQ ID NO: 10:

CAACTAGCAC TTGTTCTTCC      20